United States Patent [19]

Richter et al.

[11] Patent Number: 5,717,091

[45] Date of Patent: Feb. 10, 1998

[54] POLYCYCLIC IMINOOXADIAZINEDIONES, THEIR PREPARATION AND USE

[75] Inventors: Frank Richter, Leverkusen; Reinhard Halpaap, Odenthal; Theodor Engbert, Köln, all of Germany

[73] Assignee: Bayer Aktiengesellschaft, Leverkusen, Germany

[21] Appl. No.: 698,629

[22] Filed: Aug. 16, 1996

[30] Foreign Application Priority Data

Aug. 31, 1995 [DE] Germany .................. 195 32 060.3

[51] Int. Cl.$^6$ .................................................. C07D 498/04
[52] U.S. Cl. .................................................. 544/67
[58] Field of Search .................. 544/67; 106/313; 252/8.57, 8.61; 514/229.2

[56] References Cited

U.S. PATENT DOCUMENTS

| | | | |
|---|---|---|---|
| 4,224,431 | 9/1980 | Heiss | 528/48 |
| 4,250,106 | 2/1981 | Heiss | 260/453 SP |
| 4,495,020 | 1/1985 | Nakabayashi et al. | 156/314 |
| 5,013,838 | 5/1991 | Scholl | 544/193 |
| 5,502,147 | 3/1996 | Nodelman et al. | 528/49 |

FOREIGN PATENT DOCUMENTS

| | | |
|---|---|---|
| 081712 | 6/1983 | European Pat. Off. . |
| 728981 | 12/1942 | Germany . |

OTHER PUBLICATIONS

Wicks Jr., Progr. Org. Coatings, 3(1975) (Month unavailable) pp. 73–99.

Wicks Jr., Progr. Org. Coatings, 9(1982) (Month unavailable) pp. 3–28.

*Primary Examiner*—Mukund J. Shah
*Assistant Examiner*—Deepak R. Rao
*Attorney, Agent, or Firm*—Joseph C. Gil; Thomas W. Roy

[57] ABSTRACT

The present invention relates to polycyclic-iminooxadiazinediones corresponding to formula (I)

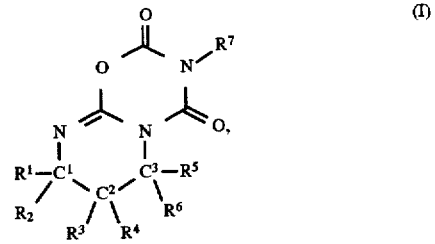

to a process for their preparation and to their use for the production of polyisocyanate addition products.

8 Claims, No Drawings

POLYCYCLIC IMINOOXADIAZINEDIONES, THEIR PREPARATION AND USE

BACKGROUND OF THE INVENTION

1. Field of the Invention

The present invention relates to new polycyclic iminooxadiazinediones, to a process for their preparation and to their use.

2. Description of the Prior Art

The reaction of isocyanates with compounds containing acidic H atoms for the production of high molecular weight substances is known (e.g. DRP 728,981) and has found wide industrial application. However, in the coatings industry low molecular weight diisocyanates can only be used to a limited extent due to their high vapor pressure. Therefore, various processes have been used for modifying these monomers for the purpose of significantly reducing the vapor pressure of the resulting products. Examples include the partial reaction of diisocyanates with dihydric and polyhydric alcohols (prepolymer formation), and the production of polyisocyanates with uretdione ("dimer"), isocyanurate ("trimer") and biuret groups.

For many applications in the coatings industry (e.g., one-component composition having a pot life which is as long as possible, polyurethane coating powder systems, aqueous systems, etc.), the high reactivity of the NCO groups of isocyanates has to be reduced, e.g., by a thermally or chemically reversible blocking of the NCO groups, using blocking agents which are split off again, possibly in modified form, during the crosslinking reaction to form the polymeric plastic or coating (e.g., Progr. Org. Coatings, 3 (1975), 73 and 9 (1981), 3). NCO groups can be reversibly blocked, for example, with ε-caprolactam, malonic acid dialkyl esters, butanone oxime, etc.

A disadvantage of using blocked isocyanates is that the blocking agents which are split off during polymerization either have to be removed during subsequent hardening or else, if they remain in the plastic or in the coating, they have a dis-advantageous effect on the property spectrum thereof (e.g., blooming and impairment of the physical and/or chemical resistance of the products).

Lacquer polyisocyanates based on uretdiones ("dimers") avoid these disadvantages, since they can undergo thermally induced cleavage to reform the (starting) isocyanates. However, uretdiones also have disadvantages. First, slow cleavage of the uretdione groups can occur during prolonged storage, particularly at elevated temperature, which results in an increase in the monomer content of the product. Second, the thermally induced splitting of the uretdione groups, which is necessary for the rapid hardening of the plastic or coating, only occurs at relatively high temperatures, which can lead to discoloration and other unwanted decomposition phenomena.

So-called self-blocked compounds of the α-nylon type, which are comparable to uretdiones, are known from EP-A 14,365. However, the cleavage of these polymers which is necessary for crosslinking occurs at even higher temperatures than required for uretdiones, which is why they have not previously been used, particularly for coating applications. Also, the thermally induced cleavage of α-nylon compounds proceeds with the evolution of monomeric diisocyanates.

An object of the present invention is to develop a composition which is capable of crosslinking, which either contains no blocking agents or contains a significantly reduced mount of blocking agents when compared to conventional compositions containing blocking agents, and which does not cleave to form monomeric diisocyanates, even at elevated temperature. An additional object of the present invention is for the highest possible amount of NCO groups present in the starting (di)isocyanate to be available for crosslinking, similar to systems containing uretdione groups.

These objects may be achieved with the polycyclic iminooxadiazinediones according to the present invention that are described hereinafter.

SUMMARY OF THE INVENTION

The present invention relates to polycyclic iminooxadiazinediones corresponding to formula (I)

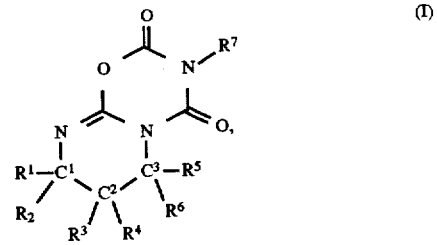

wherein $R^1$ and $R^6$ are the same or different and represent H, $C_1$–$C_{10}$-alkyl, $C_6$–$C_{24}$-cyclo-alkyl, $C_7$–$C_{24}$-aralkyl, or $C_7$–$C_{24}$-aryl, which may optionally be substituted with NCO groups, provided that $R^1$ and $R^6$, together with the $C^1$–$C^3$ carbon atoms of the iminooxadiazinedione ring system, may also form a further ring containing at least 4 C-atoms and optionally oxygen, nitrogen and/or sulfur, $R^2$ and $R^5$ are the same of different and represent H, $C_1$–$C_{10}$-alkyl, $C_6$–$C_{24}$-cyclo-alkyl, $C_{7-C24}$-aralkyl, or $C_{7-C24}$-aryl, $R^3$ and $R^4$ are the same of different and represent H, $C_1$–$C_{10}$-alkyl, $C_6$–$C_{24}$-cyclo-alkyl, $C_7$–$C_{24}$-aralkyl, or $C_7$–$C_{24}$-aryl, in which these groups may be substituted with NCO-groups and/or substituents which are not reactive with isocyanate groups, and $R^7$ represents H, $C_1$–$C_{10}$-alkyl, $C_6$–$C_{24}$-cycloalkyl, $C_7$–$C_{24}$-aralkyl, or $C_6$–$C_{24}$-aryl, in which these groups may be substituted with isocyanate groups or substituents which are not reactive with isocyanate groups, and in addition may represent a radical corresponding to formula (II)

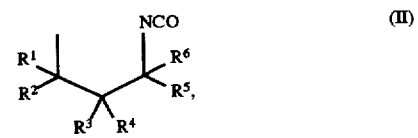

wherein $R^1$ to $R^6$ are previously defined.

The present invention also relates to a process for preparing polycyclic iminooxadiazinediones corresponding to formula (I)

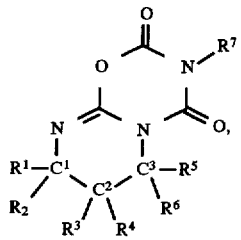

by reacting polyisocyanates corresponding to formula (III)

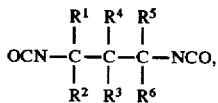

wherein $R^1$ to $R^6$ are as defined above, in the presence of a catalyst and optionally in admixture with monoisocyanates and other polyisocyanates, preferably containing 1 to 30 carbon atoms, to form iminooxadiazinediones corresponding to formula (I).

the present invention also relates to the use of the polycyclic iminooxadiazinediones of formula (I) according to the invention as an intermediate product and as a component for the production of optionally foamed polyurethane plastics, for the production of lacquers and coatings and for the production or formulation of active ingredients, pharmaceutical products, etc.

DETAILED DESCRIPTION OF THE INVENTION

The present invention is based on the surprising observation that 1,3-diisocyanates corresponding to formula (III) can be converted in the presence of a catalyst into the polycyclic iminooxadiazinediones according to the invention, optionally in the presence of other isocyanates.

This is surprising because it has been described many times in the literature that (cyclo)aliphatic 1,3-diisocyanates in the presence of various catalysts and over a wide temperature range tend to exclusively undergo (cyclo)polymerization to form high molecular weight α-nylon compounds. See, e.g. Chem. Commun. 4 (1966), 85; Organic Magnetic Resonance 2 (1970), 439; J. Makromol. Sci.-Chem. A5 (I) (1971) 37; "Organic Chemistry", A Series of Monographs, Part 2, Vol. 13 B, 2, pages 332 et seq.; and EP-A 14,365, 01.02.1979. In no case has the formation of iminooxadiazinediones been observed.

Slotta and Tschesche obtained the monocyclic trimethyl derivative 3,5-dimethyl-2-methylimino-4,6-diketo-1,3,5-oxadiazine, in addition to other products, by reacting methyl isocyanate in the presence of tributylphosphine (Chem. Ber. 60 (1927), 295 and 1011). This compound can be obtained with an improved yield when 1,2-dichloroethane is employed as a solvent (C.R. Acad. Sci. Ser. C 277 (1973) 795).

Monoyclic 3-phenyl-5-methyl-2-methylimino-4,6-diketo-1,3,5-oxadiazine, which is formally based on one equivalent of phenyl- and two equivalents of methyl isocyanate, is obtained, in addition to other products, by reacting diphenyl-methylimidocarbonate with tosyl isocyanate (Chem. Ber. 120 (1987), 339).

DE-A 3,902,078 describes the formation of a minor amount of the monocyclic tris(6-isocyanatohexyl) derivative (i.e. 3,5-bis(6-isocyanatohexyl)-2-(6-isocyanato-hexyl) imino-4,6-diketo-1,3,5-oxadiazine) by trimerizing hexamethylene diisocyanate in the presence of carbon dioxide.

The polycyclic iminooxadiiazinediones corresponding to formula (I) according to the invention can be prepared in a simple manner by the catalytically induced reaction of a polyisocyanate, preferably a diisocyanate, in which at least two isocyanate groups are disposed in the 1,3-position in relation to each other as substituents on an aliphatic polyisocyanate which is optionally substituted, which optionally contains heteroatoms, and which is optionally cyclic, wherein other mono- or polyisocyanates may optionally be used as reactants. Examples of substituents include halogen (such as Cl or Br), oxo(carbonyl), $C_1-C_{10}$-alkoxy, $C_6-C_{24}$-aryloxy, $C_1-C_{20}$-alkoxcarbonyl, and $C_6-C_{24}$-aroyl.

The compounds which are preferably used as (cyclo)aliphatic 1,3-diisocyanates are those having a molecular weight of 126 to 500, more preferably 126 to 350. Examples of these 1,3-diisocyanates include 1,3-propane diisocyanate, 1,3-butane diisocyanate, 1,3-pentane diisocyanate, 2,4-pentane diisocyanate and other isomers of the aforementioned diisocyanates in which the isocyanate groups are in a 1,3-position in relation to each other, such as 2,2-dimethylpropane 1,3-diisocyanate, for example. In the case of cycloaliphatic polyisocyanates, the ring in which the 1,3-position is directly linked with the formation of the imonooxadiazinedione structure according to the invention generally contains 4 to 8, preferably 5 or 6, most preferably 6 carbon atoms, and may contain any inert substituents, particularly alkyl groups, preferably those containing 1 to 4 carbon atoms. Preferably, in at least 20% of the polyisocyanates the isocyanate groups have a cis-configuration in relation to each other.

Preferred 1,3-diisocyanatocycloalkanes are those which contain one or more $C_1-C_4$-alkyl substituents in the 2- and/or 4-position. These cycloalkanes may be substituted by the previously described substituents that are inert to isocyanate groups. Examples of suitable 1,3-diisocyanatocycloalkanes include 1,3-diisocyanatocyclobutane, 1,3-diisocyanatocyclopentane, 1,3-diisocyanatocyclohexane, 1,3-diisocyanatocyclooctane, 1,3-diisocyanato-2-methyl-cyclohexane and/or 1,3-diisocyanato-4-methylcyclohexane, 1,3-diisocyanato-2-isopropylcyclohexane, 1,3-diisocyanato-4-isopropylcyclohexane, 1,3-diisocyanato-2,3-dimethylcyclohexane, 1,3-diisocyanato-2,4-diethylcyclohexane, 1,3-diisocyanato-2,4-diethyl-6-methylcyclohexane and/or 1,3-diisocyanato-2-methyl-4,6-diethylcyclohexane, 1,3-diisocyanato-2,4,6-triisopropylcyclohexane and 1,3-diisocyanato-2,4,6-tributylcyclohexane.

The 1,3-diisocyanates are known compounds, which can be prepared, for example, by gas phase phosgenition of the diamines on which they are based. This gas phase phosgenation is described, e.g., in DE-A 4,412,327.2. 1,3-diisocyanato-4-isopropylcyclohexane (mixture of stereoisomers) may be obtained, for example, from 1,3-diamino-4-isopropylcyclohexane (mixture of isomers) by gas phase phosgenation, and is produced in almost quantitative yield as a colorless liquid having a boiling range of 120° to 126° C. at a pressure of 0.1 mbar.

Diisocyanates obtained by phosgenation of the corresponding cycloaliphatic 1,3-diamines often occur as mixture of cis-trans stereoisomers (with respect to the position of the two isocyanate groups in relation to each other) having a cis-trans ratio of 5:1 to 1:2, preferably 3:1 to 1:1, and in principle are suitable as such for the preparation of the polycyclic iminooxadiazinediones according to the invention.

Since these latter isomers, particularly when mixtures of isomers with a high proportion of trans-isomers are used, are also susceptible to other modification reactions, such as trimerization to form isocyanurate groups, carbodiimide formation, and dimerization to form uretdione groups, for example, the polycyclic iminooxadiazinediones corresponding to formula (I) may also be produced in admixture with other by-products. They may also be produced in addition to (cyclo)polymers (α-nylon compounds), from which they may be separated if desired, e.g. by extraction.

The polycyclic iminooxadiazinediones according to the invention can also be obtained in pure form by starting from 1,3-diisocyanatoalkanes or, in the case of the cycloaliphatic representatives, from pure 1,3-cis-diisocyanatocycloalkanes. The latter may be prepared by the thermally induced depolymerization of cyclopolymeric α-nylon compounds, e.g. according to EP-A 14,365.

The process according to the invention may be conducted in the presence of a homogeneous or heterogeneous catalyst. In principle, all of the compounds cited in the literature for the preparation of oligoisocyanates having an isocyanurate or uretdione structure are suitable for use as the homogeneous catalyst. Examples include trialkylphosphines, quaternary ammonium salts such as trimethylbenzylammonium hydroxide and Si-N compounds such as hexamethyldisilazane. Also see J. Pract. Chem. 336 (1994), 185.

All of the compounds which are known for the formation of uretdione ("dimerization") and for the preparation of isocyanurates from isocyanates are also suitable as catalysts fixed to supports (heterogeneous catalysis), e.g., the preceding compounds, which are adsorptively bonded to support materials such as $Al_2O_3$ or silica gel, or particularly those which are polymerically bonded to styrene. Examples of these have been previously described in EP-A 0,447,516 or WO 93/18014.

The reaction may be conducted in the presence or absence of solvents, and may optionally be conducted at a pressure other than normal pressure. The process is preferably conducted at a temperature of $-20°$ C. to $600°$ C., more preferably $20°$ C. to $450°$ C. If solvents are employed, preferred solvents are those which boil above $150°$ C. at the pressure employed. The reaction may optionally be conducted under an inert gas, e.g. argon, nitrogen, etc.

The reaction can be stopped after the desired degree of conversion of the monomeric compound(s), for example by the addition of a catalyst poison, by thermal deactivation of the catalyst or simply by cooling the reaction mixture. In the latter case, it should be ensured when selecting the catalyst that when passing through the critical temperature range for α-nylon formation the catalyst no longer has sufficient (residual) activity or that this temperature range is passed through sufficiently rapidly ("quenching"), so that portions of unreacted monomers which may be possibly present do not react, or only react to an extent which is tolerable for the application of the product concerned, to form cyclopolymeric α-nylon. If the reaction is conducted until there is substantially complete consumption of the 1,3-diisocyanatoalkanes, problems of this type do not have to be reckoned with. The product may subsequently be separated from residual unreacted monomers by other prior art methods, such as distillation, thin film distillation or extraction.

According to a particular embodiment of the process, which may optionally be operated continuously, the reaction may be conducted in a tubular reactor. The use of catalysts fixed to supports is advantageous for this purpose, so that after the catalytically induced production of the polycyclic iminooxadiazinediones according to the invention no catalyst deactivation is necessary, which would not be the case for homogeneous catalysts.

The polycyclic iminooxadiazinediones corresponding to formula (I) may, optionally in admixture with other reaction products of isocyanates, be isolated by conventional prior art methods, such as thin film distillation, extraction, crystallization or molecular distillation, for example, and are then obtained as colorless or slightly colored liquids or solids. The latter have a melting range of about $30°$ to $150°$ C., regardless of the isocyanate (mixtures) used.

The polycyclic iminooxadiazinediones according to the invention are extremely valuable raw materials, which are suitable both as intermediates for the production or formulation of active ingredients and for use in the plastics or coatings industries.

They may be used in their pure state or in combination with other known polyisocyanate derivatives containing uretdione, biuret, allophanate, isocyanurate, urethane and/or carbodiimide groups. The NCO groups may optionally the deactivated with known blocking agents.

A particular advantage of the polycyclic iminooxadiazinediones according to the invention is that they exhibit no tendency, even during long-term thermal loading, to cleave back to the monomeric (di)isocyanates on which they are based. They also have a sufficiently high reactivity towards compounds which contain Zerewitinoff-active hydrogen. These observations are surprising, inasmuch as it is known that the heterocyclic ring system of isomeric isocyanurates is extremely inert. Moreover, there is only one reference in the literature to the fact that the iminooxadiazinedione ring can undergo a solvolysis reaction (Chem. Ber., 60(1927), 295).

If the radicals $R^1-R^7$ carry other reactive groups, for example isocyanate groups, the polycyclic iminooxadiiaz-inediones corresponding to formula (I) are preferably employed for applications with a dual crosslinking mechanism. For this purpose, for example, the free reactive group (s), e.g. isocyanate groups, are reacted in a first reaction step with a component Z containing isocyanate-reactive groups. This is similar to the so-called "pre-extension" of diols or polyols with other compounds which are at least difunctional. Crosslinking is conducted in an independent, second step with the decomposition of the iminooxadiazinedione structure. In this connection it has been shown that up to two reactants which contain Zerewitinoff-active hydrogen can be bonded for each equivalent of iminooxadiazinedione unit. In principle, any desired functionality can therefore be obtained by the presence of further reactive groups in the molecule of the polycyclic iminooxadiazinediones corresponding to formula (I) or by a corresponding modification in the aforementioned "pre-extension step" in the presence of a component Z which is more than monofunctional.

The resulting plastics and coatings have similar chemical properties to polyisocyanates containing biuret or allophanate groups based on (cyclo)aliphatic diisocyanates. Therefore, they are extraordinarily high-quality products which have the properties of the prior art compositions without the aforementioned disadvantages.

The polycyclic iminooxadiazinediones according to the invention are suitable for use as binders in coating compositions. They are preferably used as a crosslinking component, optionally in admixture with other known raw materials, and optionally in "pre-extended" form as mentioned above, in one- and two-component coating compositions, which may optionally be aqueous. When used as a crosslinking component in two-component coatings, the polyisocyanates according to the invention are generally combined with compounds containing the OH and/or NH groups known in the art. Examples include hydroxy-functional polyesters, polyethers, polycarbonates, polyurethanes and polyacrylates, as well as polyfunctional amines.

In addition to the products according to the invention and the other binder components previously disclosed, the coating compositions may also contain lacquer solvents such as toluene, xylene, cyclohexane, chlorobenzene, butyl acetate, ethyl acetate, ethyl glycol acetate, methoxypropyl acetate, acetone, white spirit, higher substituted aromatics (solvent naphtha solvents, Solvesso solvents, Shellsol solvents, Isopar solvents, Nappar solvents and Diasol solvents). Other additives include wetting agents, flow agents, skin preventing agents, antifoaming agents, matting agents, viscosity regulating substances, pigments, colorants, UV absorbers, and thermal and oxidation stabilizers.

Coating compositions based on the polycyclic iminooxadiazinediones according to the invention may be employed for coating various substrates such as wood, plastics, leather, metal paper, concrete, masonry, ceramics and textiles.

EXAMPLES

In the following examples parts and percentages are percentages by weight, unless otherwise indicated.

Example 1

200 g of hexahydrotoluene diisocyanate ("$H_6TDI$": a mixture of positional and stereo isomers of 1,3-diisocyanato-2-(or 4-)methylcyclohexane with a 2/4 positional isomer ratio of about 1:4 and containing about 60% of 1,3-cis-stereo isomers) was introduced at room temperature into a 1 liter four-neck flask with a mechanical stirrer, an internal thermometer, a reflux condenser and a metering device for the catalyst, and degassed at a pressure <1 mbar. 0.25 g corresponding to 125 ppm, of a 10% solution of benzyltrimethyl ammonium hydroxide in 2-ethyl-1,3-hexanediol were then added dropwise at 60° C. After stirring for two hours at this temperature, the mixture was heated to 75° C. and the same amount of catalyst solution was added again. The internal temperature of the mixture was kept below 100° C. by removing the heat source and applying external cooling using a water bath. After stirring for a further one hour the titrimetrically determined NCO content of the mixture had fallen to 30.3% from 46.6% initially. The reaction was then terminated by the addition of 70 mg of dibutyl phosphate, and the cooled mixture was introduced into 800 ml of dried n-hexane with vigorous stirring. After filtering off the precipitated white solid ($H_6TDI$-α-nylon), the filtrate was freed from solvent and unreacted monomer by distillation and the colorless residue, which was solid at room temperature, was analyzed:

| | |
|---|---|
| yield: | 7,1 g |
| titrated "NCO" content: according to DIN 53 185 at room temperature; | 21.1% when titrated against dibutylamine 13.4% when titrated at 0° C.; | content of tricyclic $H_6TDI$-iminooxadiazinedione (mixture of isomers) determined by gel permeation chromatography: 85%.

The identity of the compound followed unequivocally from the results of the following analytical tests: GPC, IR (also preparative GPC-IR as a coupled method), $^{13}C$ NMR, mass spectroscopy (also GC-MS as a coupled method) and elemental analysis.

Example 2

Example 1 was repeated except that 0.4 g, corresponding to 100 ppm, of a 5% solution of trimethyl-2-hydroxypropyl ammonium hydroxide in methanol was used as the catalyst and the reaction was terminated when the NCO content of the mixture, determined titrimetrically, was 32.1%. Yield after work-up as described above; 9.4 g; "NCO" content (DIN 53 185) 21.1%, content of tricyclic $H_6TDI$-iminooxadiazinedione (mixture of isomers) determined by gel permeation chromatography: 72%.

Example 3

520 g of 1,3-diisocyanato-4-isopropylcyclohexane ("$H_6CDI$", a mixture of four stereoisomers, containing about 50% of 1,3-cis-stereo isomers) was reacted as described in Example 1 with 6.4 g, corresponding to 60 ppm, of a 0.5% solution of benzyltrimethyl ammonium hydroxide until the mixture had a titrated NCO content of 30.4% (initial value: 40.4%). The reaction was terminated and the product was worked up as described in Example 1. 28.3 g of an almost colorless residue was obtained, which was solid at room temperature and had a content of tricyclic $H_6CDI$ iminooxadiazinedione (mixture of isomers) determined by gel permeation chromatography of 68%.

Example 4

100 g of 1,3-diisocyanato-2,4-diethyl-6-methylcyclohexane ("$H_6DETDI$", a mixture of several stereoisomers, containing >30% of 1,3-cis-stereo isomers) was reacted as described in Example 1 with 0.7 g, corresponding to 350 ppm, of a 5% solution of benzyltrimethyl ammonium hydroxide until the mixture had a titrated NCO content of 30.4% (initial value: 40.4%). The reaction was then stopped and the product was worked up as described. 8.2 g of a colorless residue was obtained, which was solid at room temperature, and which had a content of tricyclic $H_6CDI$-iminooxadiazinedione (mixture of isomers) determined by gel permeation chromatography of 68%.

Example 5

After degassing, 100 g of the "$H_6TDI$" described in Example 1 were heated over a short period to 260° C. in an oil bath, and 160 mg, corresponding to 640 ppm, of a 40% solution of benzyltrimethyl ammonium hydroxide in methanol were added. After stirring for fifteen minutes at this temperature, the reaction was terminated by the addition of 80 mg of dibutyl phosphate and the mixture was cooled. The NCO content of the mixture obtained was stable, although it still contained about 50% of monomeric "$H_6TDI$". After removing the monomer by distillation, 27 g of a solid residue was obtained, which contained about 30% tricyclic $H_6TDI$-iminooxadiazinedione (mixture of isomers) in addition to other $H_6TDI$ reaction products, mainly isocyanurate group-containing polyisocyanates. The NCO content of the solid resin determined according to DIN 53 185 was 23.9%.

The mixture was readily soluble in butyl acetate, methoxypropyl acetate/xylene mixture (1:1) and Solvesso 100 solvent, which are conventional coating solvents. The solutions also exhibited good compatibility with lacquer polyols.

Example 6

(Example of Application)

10 g of the polyisocyanate mixture obtained in Example 5 were mixed with 12.3 g of an OH-functional polyester (prepared from phthalic anhydride and trimethylol-propane and having an OH number of 260 and an equivalent weight of 215 g/equiv$_{OH}$) and 15 g of n-butyl acetate (NCO:OH equivalent ratio 1:1), applied to a glass plate at a thickness of 180 μm, and subjected to forced drying for 30 minutes at 80° C. A hard, clear coating was obtained, which was only slightly etched after 80 double rubs with acetone.

When a 10% excess of the OH-functional polyester component was used (which if used with known isocyanate hardeners would result in a significant deterioration of the lacquer properties of the coating) and when crosslinking was conducted for 60 minutes at 120° C., a clear coating was obtained which gave no indication of etching even after 150 double rubs with acetone. This result can be attributed to the improved crosslinking which occurred as a result of the ring opening of the iminooxadiazinedione rings at elevated temperature.

It was shown in model tests with dibutylamine or methanol that the iminoxadiazinedione unit was capable of bonding up to 2 equivalents of an NH— or OH— functional component.

Example 7
(example of application)

The polyisocyanate mixture obtained in Example 1 had a residual "$H_6TDI$" monomer content of ≦0.03%. After heating for 2 hours at 180° C., the residual monomer content had risen only slightly to 0.04%. This test verified that the "$H_6TDI$" dimer with a tricyclic iminooxadiazinedione structure (about 85% of the mixture) showed no tendency to cleave back to the starting isocyanates on which it was based. Therefore, the iminooxadiazinediones according to the invention are extremely stable to reverse cleavage, in contrast to known compounds containing uretdione groups, such as those prepared from hexamethylene diisocyanate or isophorone diisocyanate. The quantitative determination of the uretdione content of these latter compounds is frequently effected by "hot titration", since completely cleavage of the uretdione rings can be assumed at 180° C. (see DE 3,739, 549).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polycyclic iminooxadiazinedione corresponding to formula (I)

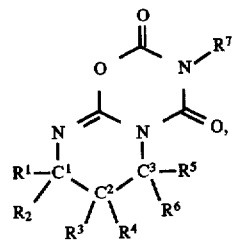

wherein $R^1$ and $R^6$ are the same or different and represent H, $C_1$–$C_{10}$-alkyl, $C_6$–$C_{24}$-cycloalkyl, $C_7$–$C_{24}$-aralkyl, or $C_7$–$C_{24}$-aryl, which may optionally be substituted with NCO groups, provided that $R^1$ and $R^6$, together with the $C^1$–$C^3$-carbon atoms of the iminooxadiazinedione ring system, may also form a further ring containing at least 4 C-atoms and optionally oxygen, nitrogen and/or sulfur, $R^2$ and $R^5$ are the same of different and represent H, $C_1$–$C_{10}$-alkyl, $C_6$–$C_{24}$-cycloalkyl, $C_7$–$C_{24}$-aralkyl, or $C_7$–$C_{24}$-aryl, $R^3$ and $R^4$ are the same or different and represent H, $C_1$–$C_{10}$-alkyl, $C_6$–$C_{24}$-cycloalkyl, $C_7$–$C_{24}$-aralkyl, or $C_7$–$C_{24}$-aryl, in which these groups may be substituted with NCO-groups and/or substituents which are not reactive with isocyanate groups, and $R^7$ represents H, $C_1$–$C_{10}$-alkyl, $C_6$–$C_{24}$-cycloalkyl, $C_7$–$C_{24}$-aralkyl, or $C_6$–$C_{24}$-aryl, in which these groups may be substituted with isocyanate groups or substituents which are not reactive with isocyanate groups, and in addition may represent a radical corresponding to formula (II)

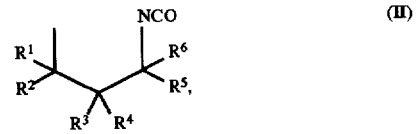

wherein $R^1$ to $R^6$ are previously defined.

2. The polycyclic iminooxadiazinedione of claim 1 wherein $R^1$ and $R^6$ are the same or different and represent H, $C_1$–$C_{10}$ alkyl, $C_6$–$C_{24}$ cycloalkyl, $C_7$–$C_{24}$ aralkyl, or $C_7$–$C_{24}$ aryl, which may optionally be substituted with NCO groups, provided that $R^1$ and $R^6$, together with the $C^1$–$C^3$ carbon atoms of the iminooxadiazinedione ring system, may also form a further ring containing at least 4 C atoms.

3. The polycyclic iminooxadiazinedione of claim 1 wherein $R^1$ and $R^6$, together with the $C^1$–$C^3$ carbon atoms of the iminooxadiazinedione ring system, form a further ring containing 6 C atoms.

4. A process for preparing polycyclic iminooxadiazinediones corresponding to formula (I)

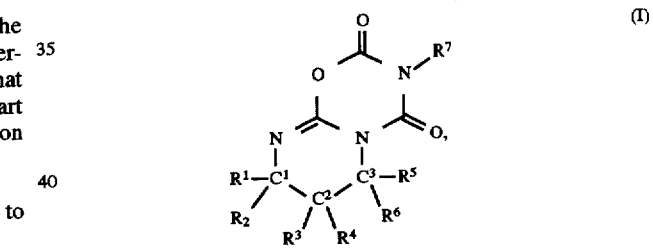

wherein $R^1$ and $R^6$ are the same or different and represent H, $C_1$–$C_{10}$-alkyl, $C_6$–$C_{24}$-cycloalkyl, $C_7$–$C_{24}$-aralkyl, or $C_7$–$C_{24}$-aryl, which may optionally be substituted with NCO groups, provided that $R^1$ and $R^6$ together with the $C^1$–$C^3$-carbon atoms of the iminooxadiazinedione ring system, may also form a further ring containing at least 4 C-atoms and optionally oxygen, nitrogen and/or sulfur, $R^2$ and $R^5$ are the same of different and represent H, $C_1$–$C_{10}$-alkyl, $C_6$–$C_{24}$-cycloalkyl, $C_7$–$C_{24}$-aralkyl, or $C_7$–$C_{24}$-aryl, $R^3$ and $R^4$ are the same of different and represent H, $C_1$–$C_{10}$-alkyl, $C_6$–$C_{24}$-cycloalkyl, $C_7$–$C_{24}$-aralkyl, or $C_7$–$C_{24}$-aryl, in which these groups may be substituted with NCO-groups and/or substituents which are not reactive with isocyanate groups, and $R^7$ represents H, $C_1$–$C_{10}$-alkyl, $C_6$–$C_{24}$-cycloalkyl, $C_7$–$C_{24}$-aralkyl, or $C_6$–$C_{24}$-aryl, in which these groups may be substituted with isocyanate groups or substituents which are not reactive with isocyanate groups, and in addition may represent a radical corresponding to formula (II)

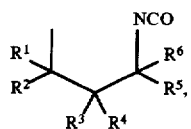

wherein $R^1$ to $R^5$ are previously defined, which comprises reacting a polyisocyanate corresponding to formula (III)

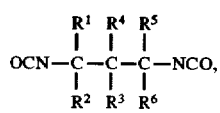

wherein $R^1$ to $R^6$ are as previously defined, in the presence of a catalyst and optionally in admixture with monoisocyanates and another polyisocyanate to form an iminooxadiazinedione corresponding to formula (I).

5. The process of claim 4, wherein the reaction is conducted at a temperature of $-20°$ C. to $600°$ C.

6. The process of claim 4, wherein the reaction is conducted at a temperature of $20°$ C. to $450°$ C.

7. The process of claim 4, wherein said polyisocyanate comprises polyisocyanates in which at least two isocyanate groups are disposed in the 1,3-position in relation to each other as substituents on an alicyclic ring system and in at least 20% of the polyisocyanates the isocyanate groups have a cis-configuration in relation to each other.

8. A coating composition comprising the product of claim 1 and an isocyanate-reactive component.

* * * * *